US00PP28500P3

(12) United States Plant Patent
Olesen

(10) Patent No.: US PP28,500 P3
(45) Date of Patent: Oct. 10, 2017

(54) MINIATURE ROSE PLANT NAMED 'POULPAR086'

(50) Latin Name: ***Rosa* hybrid**
Varietal Denomination: Poulpar086

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 15 days.

(21) Appl. No.: 14/756,259

(22) Filed: Aug. 20, 2015

(65) Prior Publication Data

US 2017/0055385 P1 Feb. 23, 2017

(51) Int. Cl.
*A01H 5/02* (2006.01)

(52) U.S. Cl.
USPC ..... Plt./118

(58) Field of Classification Search
USPC ..... Plt./118
See application file for complete search history.

(56) References Cited

PUBLICATIONS

Indoor Roses by Poulsen Main Varieties 2013.*
PLUTO Plant Variety Database Aug. 10, 2016.*

* cited by examiner

*Primary Examiner* — Annette Para

(57) ABSTRACT

A new garden rose plant of the miniature class which has abundant, light yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulpar086'.

SUMMARY OF THE INVENTION

The present discovery constitutes a new and distinct variety of miniature rose plant which was discovered in a cultivated area in 2007. The new rose variety resulted from a naturally occurring mutation of unknown causation on a branch of 'Poulpar071', U.S. Plant Pat. No. 24,549. The resulting mutation was selected and evaluations were conducted on the resulting rose plants in a controlled environment.

The rose plant of the present discovery has a unique combination of characteristics which are outstanding in the new variety and which distinguish it from the original rose 'Poulpar071' as well as all other varieties which we are aware of. For example, 'Poulpar071' has a flower color general tonality of Orange Red Group 32B while the new variety 'Poulpar086' has Yellow Group 8C to Yellow Group 13C flowers.

The criteria used to evaluate the claimed plant were selected in order to introduce a distinct variety for garden use with unique qualities, such as:

1. Uniform and abundant light yellow flowers;
2. Vigorous, but compact growth when propagated on its own roots;
3. Exceptional disease resistance.

This combination of qualities is not present in previously available commercial cultivars of this type, known to the inventor, and distinguish 'Poulpar086' from all other varieties of which we are aware.

Asexual reproduction of 'Poulpar086' by vegetative cuttings was first done by Mogens N. Olesen in Fredensborg, Denmark, in July of 2007. This initial and other subsequent propagations have demonstrated that the characteristics of 'Poulpar086' are stable and reproduced true to type in successive generations of asexual reproduction.

DESCRIPTION OF THE DRAWING

The accompanying color illustration shows as true as is reasonably possible to obtain in color photographs of this type, the typical characteristics of the buds, flowers, leaves, and stems, of 'Poulpar086'. Illustrated in FIG. 1 is are open flower, petals detached, leaves, flower buds, sepals detached, and bare stem.

DETAILED DESCRIPTION OF THE VARIETY

Figure 1:
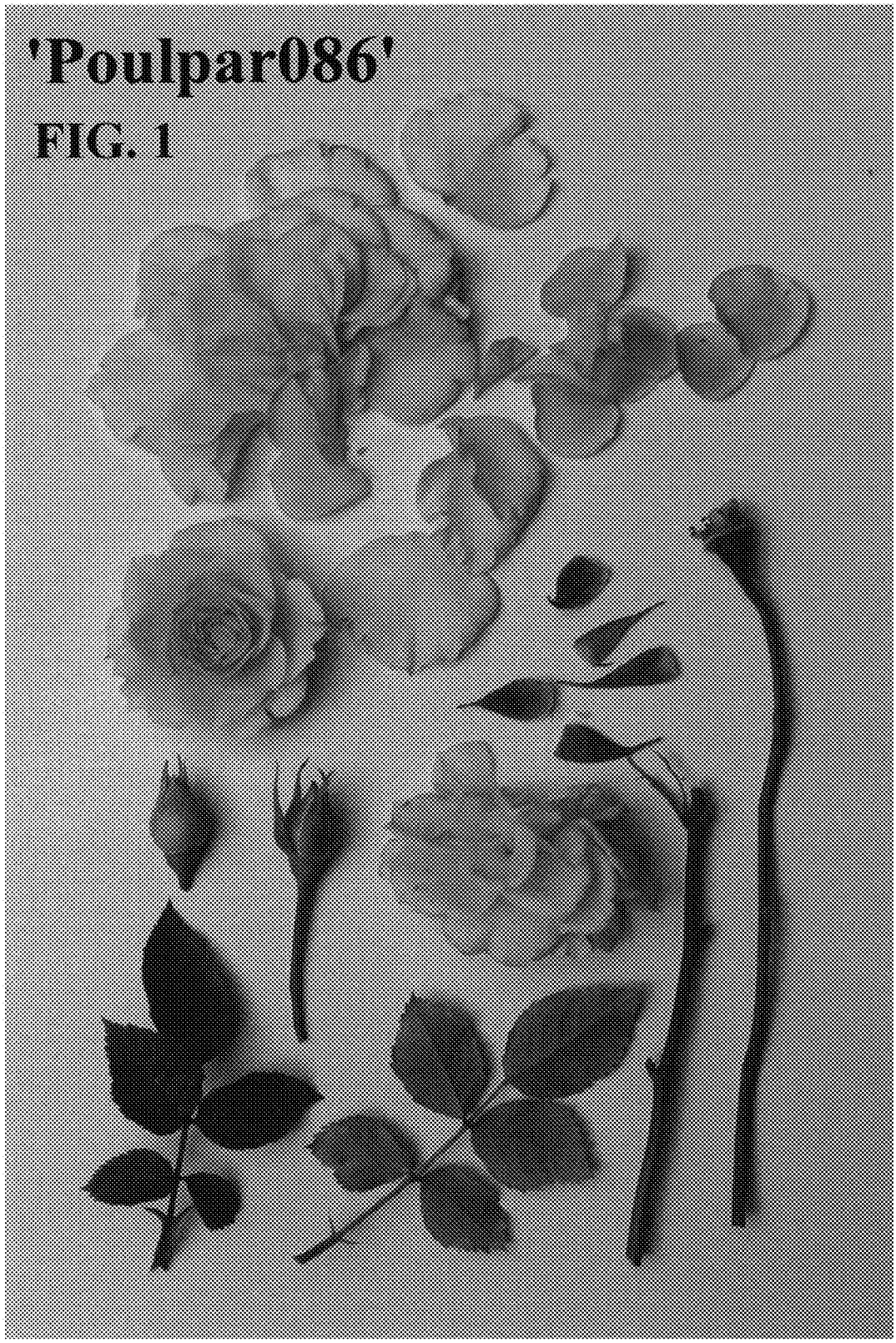
Figure 2:
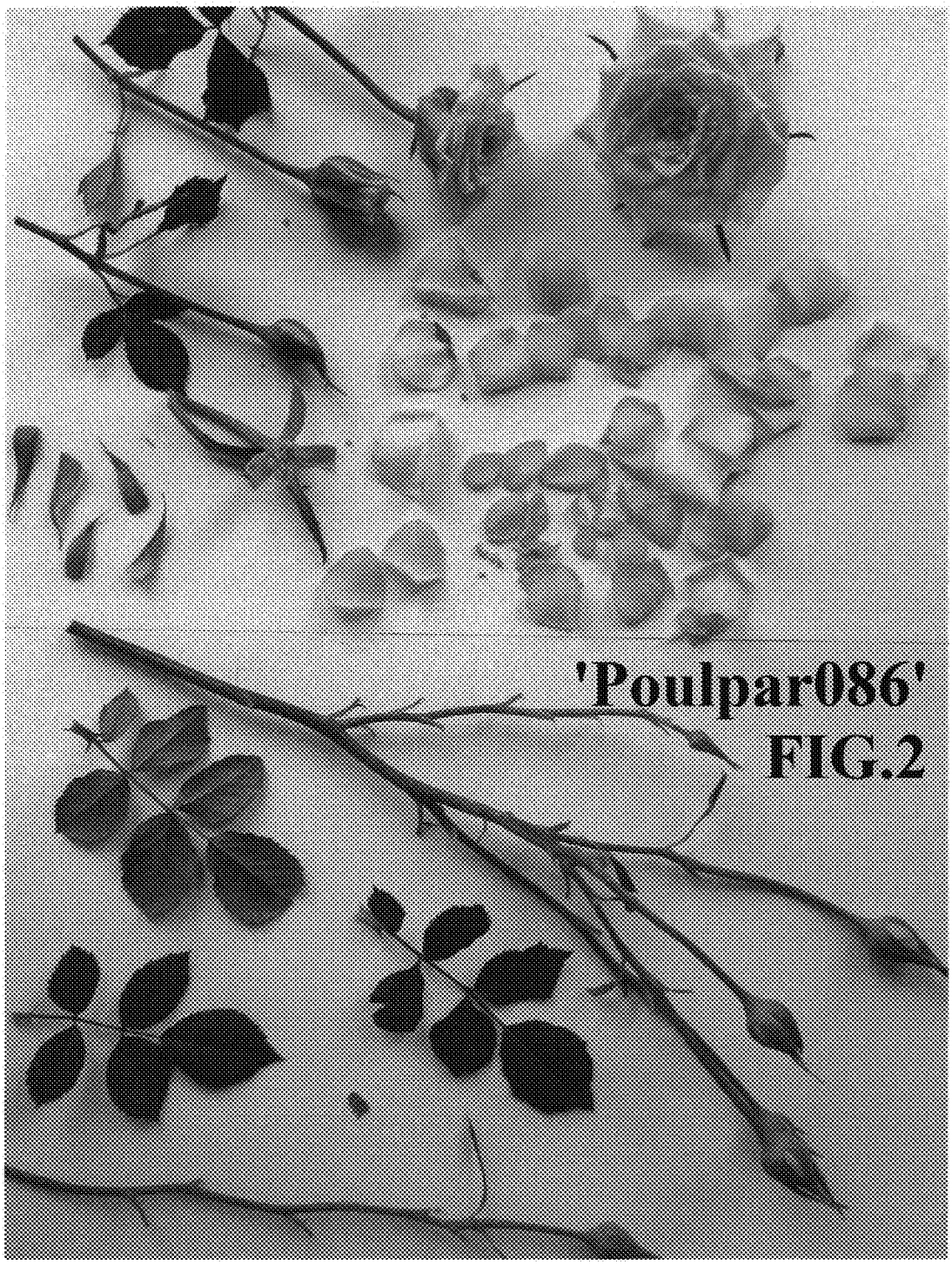
FIG. 2 shows bare stems, leaves, flower buds attached to the stem, and flowers at various stages of development.

The following is a description of 'Poulpar086', as observed in its growth in in a field nursery in Marion County, Oreg. Observed plants are 1 years of age, and were grown on their own roots. Color references are made using The Royal Horticultural Society (London, England) Colour Chart, 2001, except where common terms of color are used.

For a comparison, several physical characteristics of the rose variety 'Poulpar065', U.S. Plant Pat. No. 23,822 are compared to 'Poulpar086' in Chart 1.

CHART 1

| | 'Poulpar086' | 'Poulpar065' |
|---|---|---|
| Petal Count | 50 petals | 80 to 90 petals |
| Flower Diameter | 45 to 50 mm | 50 to 55 mm |
| General Tonality of Flower Color | Yellow Group 8C to Yellow Group 13C | Yellow Group 10B |

FLOWER AND FLOWER BUD

Blooming habit: Continuous.

Flower bud:

*Size*.—Upon opening, 20 mm in length from base of receptacle to end of bud. Bud diameter is 10 mm.

*Bud form*.—Ovoid.

*Bud color*.—As sepals divide petals are Yellow-Orange Group 16A.

*Sepal inner surface*.—Color: Yellow-Green Group 147C with intonation of Greyed-Red Group 179A. Surface: Lightly pubescent.

*Sepal outer surface*.—Color: Yellow-Green Group 144B with intonations of Greyed-Orange Group 173A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—22 mm long, 6 mm wide.

*Receptacle*.—Texture: Smooth. Size: 5 mm in height, 6 mm wide. Color: Yellow-Green Group 144B with intonations of Greyed-Purple Group 187B. Shape: Campanulate.

*Pedicel*.—Surface: Smooth. Length: 27 mm. Diameter: 2 mm on average. Color: Yellow-Green Group 144B with intonations of Greyed-Purple Group 185B. Strength: Strong.

Flower bud development: Flower buds are borne singly or in clusters of 3 flower buds per stem.

Flower bloom:

*Fragrance*.—Moderate fruity scent.

*Duration*.—The blooms have a duration on the plant of approximately 21 days. Petals fall cleanly away from plant after flowers have fully matured.

*Size*.—Flower diameter is 45 to 50 mm when open. Flower depth is 15 mm.

*Flower shape*.—High centered, double, with a high pointed center which is tightly closed.

*Shape of flower, side view*.—The upper portion is convex. The lower portion is concave.

Petalage: Under normal conditions, flowers have 50 petals total, about 5 of which are petaloids.

General tonality of flower: Open flowers are Yellow Group 8C to Yellow Group 13C.

Petal color:

*Upon opening, outer petals*.—Upper surface: Yellow Group 13C. Lower surface: Yellow Group 14C.

*Upon opening, inner petals*.—Upper surface: Yellow Group 12B. Lower surface: Yellow Group 12A.

*Basal petal spots, upon opening*.—No distinctive coloration at the petal base observed.

*After opening, outer petals*.—Upper surface: Yellow Group 4C. Lower surface: Yellow Group 10C.

*After opening, inner petals*.—Upper surface: Yellow Group 4C. Lower surface: Yellow Group 6C.

*Basal petal spots, after opening*.—No distinctive coloration at the petal base observed.

Petals:

*Petal reflex*.—Slightly reflexed.

*Margin*.—Small point at the apex of the margin. There are moderate undulations of margin.

*Shape*.—Generally broad elliptical. Apex shape: Rounded. Base shape: Obtuse.

*Size*.—About 28 mm (l)×31 mm (w).

*Texture*.—Smooth.

*Thickness*.—Average.

Petaloids:

*Size*.—15 mm (l) by 10 mm (w).

*Quantity*.—About 5.

*Shape*.—Apex is rounded, base is acute.

*Color*.—Upper surface is Yellow Group 12B. Lower surface is Yellow Group 12A.

Reproductive flower parts:

*Pollen*.—None observed.

*Anthers*.—Size: 1 mm in length. Color: Yellow Group 11B. Quantity: 20 on average.

*Filaments*.—Color: Yellow Group 13C. Length: 3 mm.

*Pistils*.—Length: 2 to 3 mm. Quantity: 15 on average.

*Stigmas*.—Color: Greyed-Yellow Group 160D.

*Styles*.—Color: White Group N155A.

*Location of stigmas*.—Inferior in location relative to the length of the filaments and the height of the anthers.

*Hips*.—None Observed.

PLANT

Plant growth: Upright, bushy. Plants are 25 cm in height, and 25 cm wide.

Stems:

*Color*.—Juvenile growth: Yellow-Green Group 144B with intonations of Greyed-Purple Group 184B. Mature growth: Yellow-Green Group 144A.

*Length*.—On average, canes are 10 cm from the base of the plant to the flowering portion.

*Diameter*.—About 3.5 mm.

*Internodes*.—On mature canes about 35 to 40 mm between nodes.

*Surface texture*.—Young wood: Smooth. Older wood: Smooth.

Long prickles: None observed.

Plant foliage:

*Compound leaf*.—83 mm (l)×50 (w).

*Quantity*.—2 or 3 leaves per 10 cm of stem on average.

*Color of juvenile foliage*.—Upper side: Yellow-Green Group 144A. Lower side: Yellow-Green Group 144B. Anthocyanin: Greyed-Red Group 181A at the leaflet margins.

*Color of mature foliage*.—Upper side: Yellow-Green Group 147A. Lower side: Yellow-Green Group 146C.

Plant leaves and leaflets:

*Stipules*.—Size: 10 mm long, 3 mm wide. Quantity: 2 per compound leaf. Shape: Linear, slightly broad based with outward extending apices. Margins: Finely serrated. Color: Yellow-Green Group 144B.

*Petiole*.—Length: 22 mm. Diameter: 1 mm.

*Upper surface*.—Color: Yellow-Green Group 144B with intonations of Greyed-Red Group 181B.

*Lower surface*.—Color: Yellow-Green Group 144A.

*Rachis*.—Length: About 25 mm. Upper surface: Color: Yellow-Green Group 144B with intonations of Greyed-Red Group 181B.

*Lower surface*.—Color: Yellow-Green Group 144A. Observations: Small prickles.

*Leaflet*.—Quantity: Normally 5 leaflets. Margins: Serrated. Size: On average terminal leaflets are 32 mm long, 20 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpar086', substantially as illustrated and described herein, due to its abundant light yellow flowers, disease resistance, and extended period of bloom.

* * * * *

'Poulpar086'